United States Patent [19]
Ellis

[11] Patent Number: 5,990,378
[45] Date of Patent: *Nov. 23, 1999

[54] TEXTILE SURGICAL IMPLANTS

[75] Inventor: Julian Garth Ellis, Nottingham, United Kingdom

[73] Assignee: Bridport Gundry (UK) Limited, Somerset, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 08/652,316

[22] Filed: May 23, 1996

[30] Foreign Application Priority Data

May 25, 1995 [GB] United Kingdom ............ 9510624

[51] Int. Cl.$^6$ .................................................. A61F 2/02
[52] U.S. Cl. ............................ 623/11; 623/1; 623/12; 623/13; 606/151; 606/154
[58] Field of Search ................... 606/151, 153–155, 606/213–216, 228–230; 623/1, 11–15, 901, 66

[56] References Cited

U.S. PATENT DOCUMENTS

| | | | |
|---|---|---|---|
| 4,415,617 | 11/1983 | D'Elia | 428/86 |
| 4,905,692 | 3/1990 | More | 606/151 |
| 5,443,499 | 8/1995 | Schmitt | 623/12 |
| 5,458,636 | 10/1995 | Brancatao | 606/151 |

FOREIGN PATENT DOCUMENTS

| | | | |
|---|---|---|---|
| 0 117 072 A1 | 8/1984 | European Pat. Off. | 623/12 |
| 0 334 045 A1 | 9/1989 | European Pat. Off. | 623/12 |
| 0621017 | 10/1994 | European Pat. Off. | 623/1 |
| 3830005 C1 | 11/1989 | Germany | 623/11 |

*Primary Examiner*—Michael J. Milano
*Assistant Examiner*—Tram A. Nguyen
*Attorney, Agent, or Firm*—Salter & Michaelson

[57] ABSTRACT

A textile surgical implant includes a base cloth, and an array of fibers provided on the base cloth. The base cloth is removable from the fibers before or after the location of the implant in a patient. A method of making a textile surgical implant is further disclosed. The method includes the step of placing an array of fibers on a base cloth by embroidery. The base cloth is removable from the fibers before or after the implant is implanted.

25 Claims, 3 Drawing Sheets

TEXTILE SURGICAL IMPLANTS

BACKGROUND OF THE INVENTION

This invention relates to a textile surgical implant.

The manufacture of textile surgical implants often requires the manufacture of a low number of items. Modern textile manufacturing methods, however, are usually only cost effective if large numbers are produced. An advantage of high volume automatic manufacturing methods is that the articles manufactured are almost exactly alike. Such similarity is required by the needs of modern scientific surgery, in order that all patients shall be treated alike and that there is no untoward variation from implant to implant.

It is, therefore, desirable that textile implants should be able to be made cost effectively in small numbers on machinery that is mechanically or electronically controlled in such a way that each item produced to the same design will be virtually identical.

It is also desirable that the design method used shall be simple and quick to carry out, in order to minimise design costs. Low design costs also facilitate the cost-effective production of implants made to individual measurements, which may be desirable for unusual medical conditions or for use in patients where it is necessary to produce an implant of an exact size to fit that person.

Ideally a textile implant will have the textile fibres placed in a position and direction which accord with the design requirements in order that they may carry out their function correctly, whether it be load-bearing or otherwise.

The present invention is intended to deal with the above-mentioned problems.

SUMMARY OF THE INVENTION

According to the present invention there is provided a textile surgical implant comprising an array of fibres wherein the fibres forming the implant are placed in position in the implant by embroidery.

The term implant as used herein is not confined solely to implants that are intended to be surgically or otherwise implanted in the body, but also includes stents and the like such as are implanted in the oesophagus.

Embroidery is normally defined as work with a needle and thread upon cloth. In conventional embroidery the fibres are placed with a needle according to the requirements of the aesthetic design selected. In the manufacture of a textile surgical implant, the fibres can be placed according to the functional requirements of the design, for example so that one or more yarns in the structure may efficiently carry a load in an artificial ligament.

Many modern embroidery machines comprise a sewing head above an X-Y plotter. The plotter can be moved with great precision below the needle head (or vice-versa) so that the sewing head moves relative to the base cloth as required. The movements are controlled by punched card, or preferably, electronic computer control. An alternative arrangement is for the sewing head to move, whilst the base cloth remains stationary.

The definition of embroidery implies that the embroidery stitches must be made upon a base cloth. However, according to one embodiment of the present invention there is provided a base cloth that is soluble, so that after the implant is formed upon the base cloth, the cloth can be dissolved away and only the embroidered stitched structure remains. Using design rules known to those skilled in the art, embroidered structures can be made so that placed fibres of the embroidery retain their structural integrity and hold together after the base cloth has been dissolved away. The dissolution can be by aqueous medium if a water soluble base fabric is used such as a base fabric made from polyvinyl acetate, or alginate. Alternatively a solvent such as acetone may be used for example when an acetate base fabric is utilised. Other base fabrics can be used which may be removed for example with acid, alkali, or organic solvent or with water, or by heat or other method.

In one embodiment of the invention a sheet material, such as polyglycolic acid, is used which degrades or is absorbed after implantation, leaving more permanent parts of the embroidered structure within the body. The implant or the base fabric can be impregnated with one or more growth factors, or angiogenic or neurogenic materials that my stimulate the production of blood vessels, nerves, or other types of tissue around and/or into the implant.

BRIEF DESCRIPTION OF THE DRAWINGS

Specific embodiments of the invention will now be described with reference to the accompanying drawings in which.

DETAILED DESCRIPTION OF THE PREFERRED EMBODIMENTS

Figure 1:
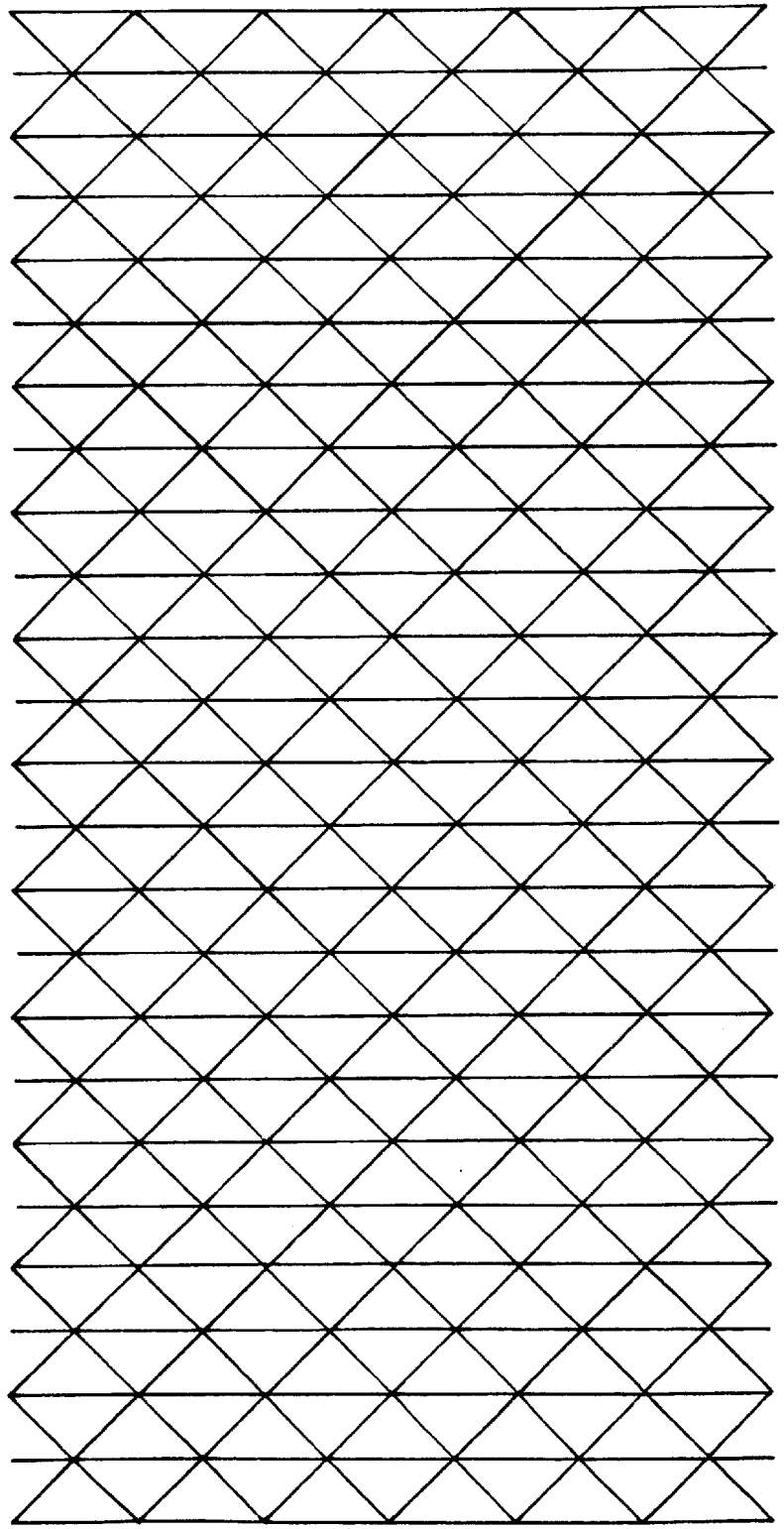
FIG. 1 is a plan view of a mesh structure.

Referring first to FIG. 1 a mesh structure comprises crossing threads which are laid substantially at right angles to each other. The interlocking may be achieved by a number of interlocking methods well known to those skilled in the art. Generally the interlocking is effected when the first laid down layer is crossed by the second laid part, when threads from the underthread and needle thread pass under and over the first laid thread and are interlocked by lockthread stitching as usually used for the embroidery. Different ways of interlock will give different load extension characteristics to the implant for different applications or different patients.

Such a mesh can be used to act as a reinforcing patch within the body. For example a patient may suffer from an incisional hernia where some of the internal tissues of the gut may protrude through the walls of the abdomen and the internal tissues are only held within the body by a thin layer of the body wall. The edges of the hernia may have weakened as a result of the hernia or from some other cause, which makes repair using conventional sutures difficult. The provision of a patch will assist the surgeon to obtain a good repair by enabling him to stitch the tissue at a site remote from the weak edges. The patch can also provide a scaffold on which a new tissue may grow. The requirements of any patch include that it shall have a high bursting strength, that it shall be easy to cut to size appropriate to the condition of the patient without fraying or unroving from the cut edges. Many woven structures have good properties with regard to bursting strength, but will fray readily from a cut edge. The use of a hot knife to cut thermoplastic fibres to prevent them from fraying is undesirable because of the inconvenience of carrying out this is operating theatre conditions and the sharp edges (and possibly toxic degradation products) that thermal cutting often leaves.

The provision of a thermoplastic monofilament patch where intersecting fibres in a mesh are thermally bonded is known, but any cut edges of the monofilament comprising the patch may be undesirably sharp and thermal bonding restricts the choice of fibres to those which are thermoplastic. The use of adhesives to bond the intersections of the mesh is inconvenient and may introduce a biologically incompatible component to the implant. According to the present invention any implantable fibre may be used, since the intersections of the mesh are stitched and are resistant to fraying when the mesh is out.

Figure 2:
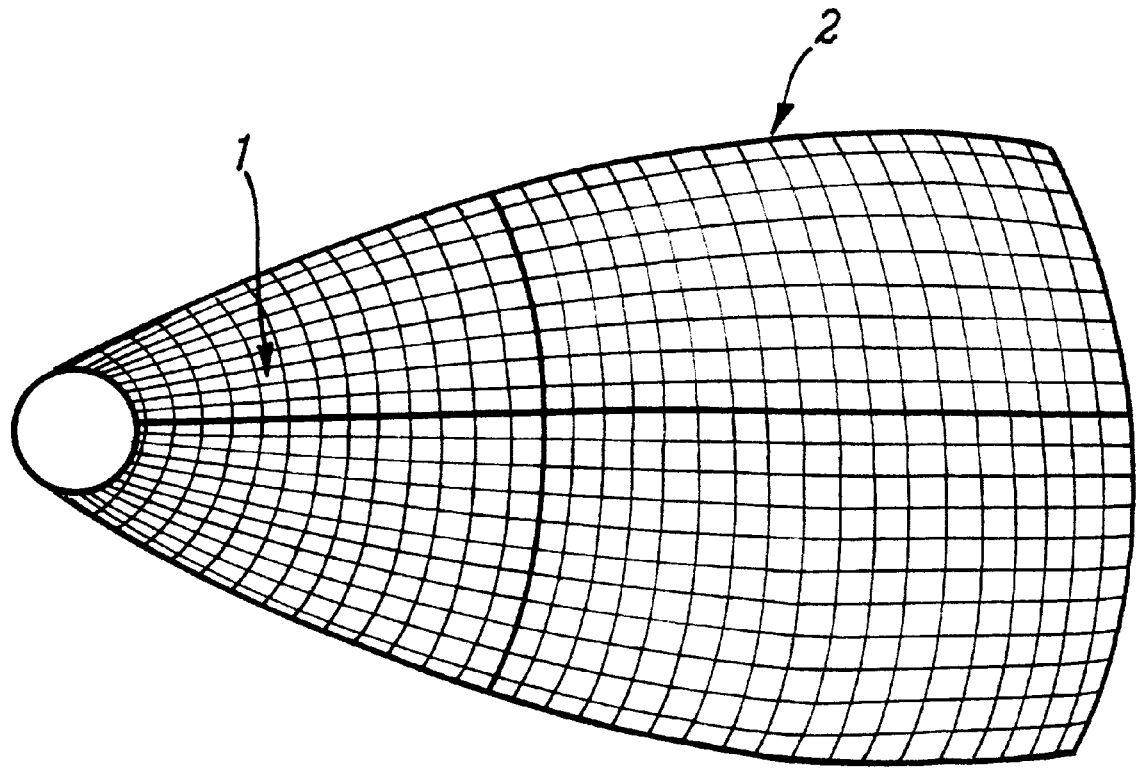
FIG. 2 is a plan view of another mesh structure suitable for repair of a tendon or ligament.

The invention provides a patch for the repair of tendon or ligament. For example the rotator cuff of the shoulder is difficult to repair without the use of textile reinforcement. Frequently a multiplicity of suture threads is used, but sometimes this method of reinforcement is insufficient and a reinforcing textile fabric is required. The use of a hood as described in PCT International Patent Appln. No. WO 91/03993 is one example. This provides a woven or knitted flexible fabric. The openness of the mesh is chosen so as to allow tissue ingrowth without being so open that the structural integrity is lost. The present invention includes the provision of an embroidered mesh, with areas of extra strength to carry localised heavier loads. One embodiment of this aspect of the invention is shown in FIG. 2. The mesh is ideally provided so that the holes are spaced approximately 2 mm apart and are approximately 1 mm square. The strength of the mesh is such that it must carry a minimum load of approximately body weight. The use of embroidery to form the mesh 1, has the advantage that the mesh can be locally reinforced using a different type of thread or higher concentration or density of treads or using a multiplicity of the same thread as illustrated by the bold lines referenced 2. In a preferred embodiment the main mesh 1 is made using a braided polyester fibre 0.35 mm in diameter and the reinforcement 2 is a polyester braid of 1.5 mm diameter.

Figure 3:
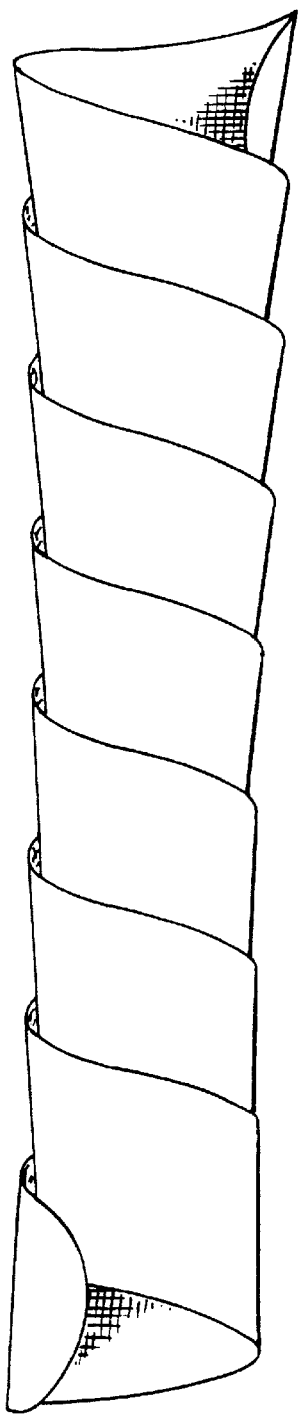
FIG. 3 illustrates a tubular stent suitable for insertion into hollow viscera.

The invention also provides an implant to form a sheet material having a different stiffness in one axis to the stiffness in the other axis. An implant of this kind, known as a stent, an example of which is disclosed in UK Patent Appln. No. CB 2270264 is in the form of a tube that can be compressed for insertion into the human or animal body to relieve blocking of the oesophagus or other hollow viscera by tumours or other disorders. If the coiled stent is made from stiff anisotropic sheet material and would up tightly to reduce its diameter in order to insert it within the oesophagus, the tube becomes so rigid that the stent becomes difficult to insert in some patients, for example elderly patients with stiff necks or protuberant teeth. FIG. 3 shows a self expanding solid walled tube similar to a coil spring tube. The tube can be would tightly to form a low diameter tube, or stent, which may be inserted into hollow viscera within the body and then allowed to expand, pushing aside any blockage of the hollow viscus that may have been caused by a tumour or other disorder. One example of an application is to patients in whom the oesophagus may have become blocked by a malignant tumour, making swallowing difficult.

In the embodiment of FIG. 3 the material forming the stent is made by laying stiff fibres in one axis direction of the stent onto a base embroidery material and the other direction with less stiff or no fibres. This results in an isotropic material that when wound tightly about an axis parallel to the said other direction into a low diameter tube for insertion within the hollow viscus is much less stiff in the length axis, yet retains its springiness in the radial direction. In the embodiment shown in FIG. 3 the stent is formed by winding a strip of fabric about an axis such that each turn other than the first slightly overlaps the preceding turn, thus forming a tube with a substantially continuous wall surface. In use the stent diameter is reduced by tightening the turns and then positioned in its desired location, for example in a hollow viscus, the lower stiffness of the stent in the axial direction making it easy to insert in position. Once in position the stent is allowed to expand within the hollow viscus, pushing aside a tumour or other obstruction, yet it retains flexibility in the length direction.

Figure 4:
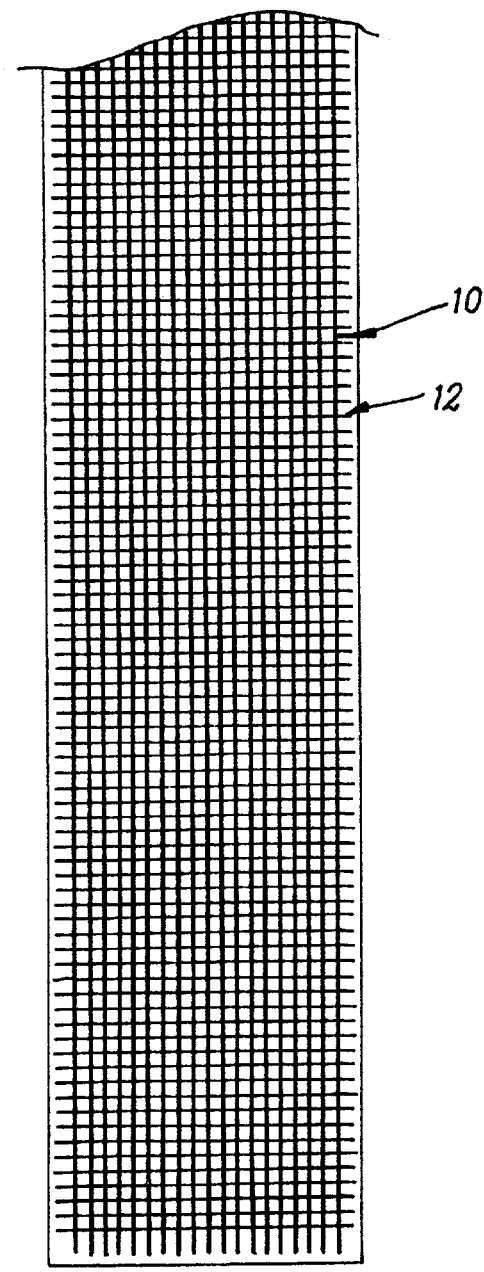
FIG. 4 shows a material which can be used, inter alia, for the stent of FIG. 3.

In a particularly preferred embodiment, the fibres are arranged as shown in FIG. 4, the longitudinal fibres 10 are monofilament polyester of high stiffness and the lateral fibres 12 are of lower stiffness monofilament polyester. If this material is coiled into a stent of the kind shown in FIG. 3 and heat-set into shape, the stent, when tightly coiled for insertion into the oesophagus of the patient, remains flexible in the longitudinal axis and may be more easily inserted.

It may be seen from the foregoing description and examples that the invention has a wide number of applications, not confined to those described herein.

What is claimed is:

1. A textile surgical implant comprising a bioabsorbable base cloth having an embroidered mesh structure disposed thereon, said base cloth being absorbed after the location of the implant in a patient.

2. An implant as claimed in claim 1, wherein the base cloth is soluble.

3. An implant as claimed in claim 1, wherein the base cloth is made from materials which will degrade after the implant is implanted in a patient.

4. An implant as claimed in claim 1, wherein the embroidered mesh structure is reinforced in at least a part thereof.

5. An implant as claimed in claim 1, wherein said implant is of substantially triangular shape.

6. An implant as claimed in claim 1, said embroidered mesh structure having fibres arranged to give greater stiffness in one direction than in another direction.

7. An implant as claimed in claim 6, comprising first fibres of a greater stiffness extending in one direction, and second fibres of a lesser stiffness extending in a second direction, the first and second directions of the fibres being substantially at right angles to one another.

8. An implant as claimed in claim 7, wherein the tube is heat set to retain its shape.

9. An implant as claimed in claim 6 formed as a tube having a radial stiffness greater than the stiffness in the axial direction.

10. An implant as claimed in claim 9, wherein the tube is formed from a strip having fibres arranged in two directions, the strip being wound about an axis.

11. An implant as claimed in claim 10, wherein the strip is wound in a plurality of turns and each turn of the strip, other than the first, overlaps the preceding turn.

12. An implant as claimed in claim 1 and comprising one or more growth factors, angiogenic and neurogenic materials.

13. A method of making a textile surgical implant comprising the step of:

embroidering a mesh structure on a bioabsorbable base cloth, said base cloth being absorbed after the implant is implanted in a patient.

14. A method as claimed in claim 13, wherein the base cloth is soluble and is removed by dissolving the base cloth in a solvent.

15. A method as claimed in claim 13, wherein the base cloth is removed by degradation after the implant has been implanted in a patient.

16. A method as claimed in claim 13 and comprising reinforcing the mesh structure in at least a part thereof.

17. A method as claimed in claim 16, wherein said mesh structure includes fibres arranged to give greater stiffness in one direction of the mesh structure than in another direction thereof.

18. A method as claimed in claim 17, wherein fibres giving grater stiffness are placed at substantially right angles to fibres giving differential stiffness.

19. A method as claimed in claim 17, wherein the mesh structures is formed as a tube having a radial stiffness greater than the stiffness in the axial direction.

20. A method as claimed in claim 19, wherein the tube is formed from a strip having fibres arranged in two directions by winding the strip about an axis.

21. A method as claimed in claim 20, wherein the strip is wound in a plurality of turns, each turn of the strip, other than the first, overlapping the preceding turn.

22. A method as claimed in claim 19 wherein the tube is heat set to retain its shape.

23. A method of making a textile surgical implant comprising the step of:

placing an array of fibers arranged as a mesh on a bioabsorbable base cloth by embroidery, said base cloth being absorbed after the implant is implanted;

wherein said fibers are arranged in the mesh to give greater stiffness in one direction of the mesh than in another direction thereof.

24. A textile surgical implant comprising a base cloth and a mesh structure of fibers provided on said base cloth by embroidery, said base cloth being made from a biocompatible material which is absorbed after the implant is implanted.

25. A method of making a textile surgical implant comprising the step of:

placing a mesh structure of fibers on a base cloth by embroidery, said base cloth being made from a biocompatible material which is absorbed after the implant is implanted.

* * * * *